(12) United States Patent
Kump

(10) Patent No.: US 7,221,782 B1
(45) Date of Patent: May 22, 2007

(54) METHOD AND APPARATUS FOR DETERMINING A DYNAMIC RANGE OF A DIGITAL MEDICAL IMAGE

(75) Inventor: Kenneth Scott Kump, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/344,190

(22) Filed: Jun. 24, 1999

(51) Int. Cl.
*G06K 9/00* (2006.01)

(52) U.S. Cl. ...................................... 382/128; 382/132
(58) Field of Classification Search ................ 382/128, 382/130–133; 378/4, 116; 128/922; 359/548; 356/39; 600/424, 425, 426, 427
See application file for complete search history.

(56) References Cited

U.S. PATENT DOCUMENTS

| | | | |
|---|---|---|---|
| 4,315,318 A | 2/1982 | Kato et al. | |
| 4,674,125 A | 6/1987 | Carlson et al. | |
| 4,716,414 A | 12/1987 | Luttrell et al. | |
| 4,718,104 A | 1/1988 | Anderson | |
| 4,943,707 A | 7/1990 | Boggan | |
| 4,969,204 A | 11/1990 | Melnychuck et al. | |
| 5,045,955 A * | 9/1991 | Ikeda ......................... | 386/100 |
| 5,187,579 A * | 2/1993 | Hiyama ....................... | 348/588 |
| 5,461,233 A * | 10/1995 | Yamamoto et al. ........ | 250/368 |
| 5,461,655 A | 10/1995 | Vuylsteke et al. | |
| 5,467,404 A | 11/1995 | Vuylsteke et al. | |
| 5,546,473 A | 8/1996 | Buytaert et al. | |
| 5,588,435 A * | 12/1996 | Weng et al. ................ | 600/443 |
| 5,616,930 A | 4/1997 | Janssens et al. | |
| 5,644,662 A | 7/1997 | Vuylsteke | |
| 5,652,776 A | 7/1997 | Riet | |
| 5,717,791 A | 2/1998 | Labaere et al. | |
| 5,832,055 A | 11/1998 | Dewaele | |
| 5,991,816 A * | 11/1999 | Percival et al. ............. | 709/247 |
| 6,162,174 A * | 12/2000 | Friemel ....................... | 600/447 |
| 6,185,271 B1 * | 2/2001 | Kinsinger ................... | 378/19 |

(Continued)

*Primary Examiner*—Duy M. Dang
(74) *Attorney, Agent, or Firm*—McAndrews, Held & Malloy, Ltd.; Peter J. Vogel; Michael A. Dellapenna

(57) ABSTRACT

A method and apparatus are provided for adjusting a dynamic range of a digital medical image for a medical imaging system. The digital medical image contains a clinical region and a non-clinical region. The method and apparatus identify the non-clinical region of the digital medical image and mask the non-clinical region therefrom to form a clinical image. The clinical image is then used to calculate a desired dynamic range for the medical imaging system. The dynamic range of the medical imaging system is adjusted accordingly. According to one embodiment, the non-clinical region is identified by dividing the digital medical image into bands of a predetermined width, generating profiles for each band and differentiating the profiles to obtain a differentiated profile of each band of a digital medical image. The differentiated profile is than analyzed to identify peaks that exceed predetermined thresholds, wherein the regions of the differentiated profile proximate the peaks exceeding the threshold correspond to non-clinical regions. Once the non-clinical regions are identified, they are masked or removed. Next, a desired image characteristic, such as maximum and minimum gray scale values, are determined for the clinical region and a desired dynamic range for the image is obtained based on the image characteristics of the clinical region. In an alternative embodiment, a histogram is used to identify the non-clinical regions which are subsequently masked from the digital medical image.

22 Claims, 5 Drawing Sheets

U.S. PATENT DOCUMENTS 6,222,907 B1 * 4/2001 Gordon ...................... 378/116
6,298,109 B1 * 10/2001 Ergun ............................ 378/4
6,351,276 B1 * 2/2002 Yamaguchi .................. 347/188
6,618,494 B1 * 9/2003 Nonay et al. ............... 382/132

* cited by examiner

METHOD AND APPARATUS FOR DETERMINING A DYNAMIC RANGE OF A DIGITAL MEDICAL IMAGE

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention generally relates to medical diagnostic imaging and in particular to a method and apparatus for determining dynamic range of a digital medical image to be displayed.

X-ray imaging had long been an accepted medical diagnostic tool. X-ray imaging systems are commonly used to capture, as examples, thoracic, cervical, spinal, cranial and abdominal images that often include the information necessary for a doctor to make an accurate diagnosis. When having a thoracic x-ray image taken, for example, a patient stands with his or her chest against an x-ray sensor as an x-ray technologist positions the x-ray sensor and an x-ray source at an appropriate height. The x-ray sensor then detects the x-ray energy generated by the source and attenuated to various degrees by different parts of the body. An associated control system scans out the detected x-ray energy and prepares a corresponding diagnostic image on a display. Optionally, the x-ray sensor may be a solid state digital image detector. If the x-ray sensor is a conventional screen/film configuration, the screen converts the x-rays to light, to which the film is exposed.

In conventional radiographic imaging systems, the x-ray technique is chosen by the operator. The operator or the automatic exposure control system selects or determines a desired exposure for the selected screen/film configuration in order to obtain a desired optical density of the exposed film. The optical density represents the "lightness" or "darkness" of the screen, detector or film once exposed to x-rays. By controlling the manner (e.g., time, orientation, etc.) of exposure by the detector, screen or film to x-rays, the film lightness or darkness may be varied. It is preferable to achieve a consistent optical density from one exposure to the next in order to facilitate diagnosis and examination by physicians when analyzing radiographic images. Different exposures arise from one patient to the next, from one film type to the next, from one medical imaging system to the next, from one orientation to the next and the like.

In the past, it has been quite difficult to maintain a uniform optical density from one exposure to the next (e.g., patient to patient, film to film, system to system, patient angle to patient angle) due to inherent differences. For instance, each patient has a slightly different size and anatomy which causes the internal organs of the patient to be located at different positions relative to the detector or screen/film. For example, when attempting to obtain an x-ray of a chest image, every patient's lungs and rib cage are of a different size. The position of the lungs is also somewhat unknown which creates a large variance in the resulting exposure. Further, patient position is not precisely controlled and hence each patient is located in a slightly different position or orientation with respect to the detector or screen/film configuration. Variation in patient position and orientation further create variance in the resulting exposure. Optical density may further be varied due to the particular pathology followed by the x-rays through the patient, due to foreign objects within a patient (e.g., pacemakers and the like) as well as due to differences in patient thickness and resulting scatter pattern properties.

An automatic exposure control has been proposed for use with radiographic systems in an attempt to control the optical density of the exposed film. Automatic exposure control systems typically use an x-ray sensitive ion chamber located proximate the detector, screen/film configuration and arranged to be proximate a particular anatomy of a patients during examination. For instance, an ion chamber may be located within a region of the detector or screen/film configuration calculated to be proximate the patient's lung during a particular form of examination. Alternatively, or in addition, an ion chamber may be located proximate the patient's mediastinum. The automatic exposure control measures the x-rays detected by the ion chamber and terminates the exposure when a preset dose is measured.

However, automatic exposure control systems have experienced difficulties. In particular, the position of an individual patient's lung is unknown at the time that the ion chamber is placed proximate the detector, screen or film. Hence, different patients continue to create a large variance in the resulting exposure to the ion chamber. For instance, the ion chambers may not actually be located proximate certain patient's lungs or mediastinum. When an ion chamber is located proximate an anatomy other than the lung or mediastinum, the automatic exposure control terminates exposure based on inaccurate measurements. A certain percentage of chest films result in creation of either too dark or too light of an image. When the image is too dark or too light, it may be necessary to repeat the x-ray examination to retake the medical image. It is quite time consuming to retake medical images. Film development may require a relatively long period of time, such as five to fifteen minutes, during which the patient may leave the image acquisition area.

Further, a resulting presentation of a medical image is determined by the selection of the type of detector, film/screen configuration in combination with the desired x-ray technique. Different types of detectors and screens/film configurations experience different amounts of image noise. In the past, noise has been partially corrected by varying the input exposure time. However, to maintain a constant optical density from one exposure to the next, when detector, film or screen types are changed, the exposure time must be changed in order to account for the fixed dynamic range of the new detector, screen/film configuration. It is quite cumbersome to change detectors, screens or films, and thus rarely done.

More recently, digital detectors have been proposed for use with radiographic imaging. Digital detectors afford a significantly greater dynamic range than convention screen/film configurations, typically as much as two to three times greater. Heretofore, the automatic exposure control and operator must still be relied upon to limit the exposure of the digital detector to account for the detectors greater dynamic range.

A need remains for an improved dynamic range detection and control method and apparatus for use with digital medical imaging, such as in radiographic imaging.

SUMMARY OF THE INVENTION

A preferred embodiment of the present invention provides a method and apparatus for determining a dynamic range of a digital medical image for a medical imaging system. The medical image contains clinical regions and non-clinical regions. The method and apparatus identify the non-clinical regions of the digital medical image and mask the non-clinical regions from the digital medical image to provide an automatic contrast control for displaying a clinical image. Once the non-clinical region has been masked, the method and apparatus determine the dynamic range for the clinical image.

According to one alternative embodiment, the non-clinical regions are identified by dividing the digital medical image into bands of predetermined width and locating the non-clinical region in each band. The bands may be aligned horizontally and/or vertically within the digital medical image. During identification, the bands of the digital medical image are differentiated and discriminated with thresholds to identify changes in gray scale along a profile corresponding to a horizontal or vertical band. A mask for masking non-clinical regions is turned on and off based on maximum and minimum peaks in the differentiated profile for the digital medical image.

In an alternative embodiment, the non-clinical regions are identified after a histogram is generated from the digital medical image. Thresholds may be obtained based on a dynamic range of the digital medical image and used to identify maximum and minimum gray scale values in the histogram associated with non-clinical regions. The non-clinical regions are masked based on the maximum and minimum values identified in the histogram as being associated with non-clinical regions.

In yet a further alternative embodiment of the present invention, a medical diagnostic imaging system is provided for determining a dynamic range of a digital medical image to be displayed. A digital detector may be provided in order to obtain the digital medical image. The digital medical image includes a clinical region and a non-clinical region. The system includes a segmentation module and a dynamic range module. The segmentation module identifies the non-clinical region in the digital medical image. The dynamic range module determines the dynamic range of the clinical region of the digital medical image once the non-clinical region has been segmented. The segmentation module may identify raw radiation regions and/or collimated regions as non-clinical regions.

In one alternative embodiment, the segmentation module identifies non-clinical regions based on variations in gray scale levels of the digital medical image. The segmentation module differentiates and threshold detects at least a portion of the digital medical image to identify the non-clinical region. In an alternative embodiment, the segmentation module generates a histogram corresponding to the digital medical image and utilizes at least one gray scale threshold value to discriminate the non-clinical region.

A processor may be included to calculate at least one threshold based on a dynamic range of the digital medical image. The dynamic range module may include a processor masking non-clinical regions when determining the dynamic range of the clinical region. A processor may be further provided to calculate at least one of a maximum and minimum gray scale level for the digital medical image in order to identify the non-clinical region. A processor may also calculate at least one of a maximum and minimum gray scale level for the clinical region in order to determine its dynamic range.

At least one preferred embodiment of the present invention frees the reliance of the system upon patient positioning and x-ray acquisition techniques in order to obtain a uniform output density for display from patient to patient, film to film and system to system. The dynamic range management methods and systems of the preferred embodiments of the present invention are equally useful in general radiographic applications and may be scalable with respect to various exposures and mean gray scale levels. A resulting image presentation may improve signal-to-noise ratio characteristics without changing a global contrast of an image, thereby taking advantage of the wide dynamic range of digital detectors.

By affording the ability to detect the diagnostic/clinical dynamic range of a digital medical image, specific knowledge is no longer required of the dose level, nor patient type. Optionally, dose level and/or patient type may be used to improve robustness. The dynamic range management methods and systems of the preferred embodiments of the present invention allow independent operation of image presentation and image acquisition, while assuring image quality and consistent presentation from image to image, patient to patient, dose to dose and system to system. The preferred embodiments of the present invention also afford the ability to simulate global contrast curves of screen/films.

DETAILED DESCRIPTION OF THE INVENTION

Figure 1:
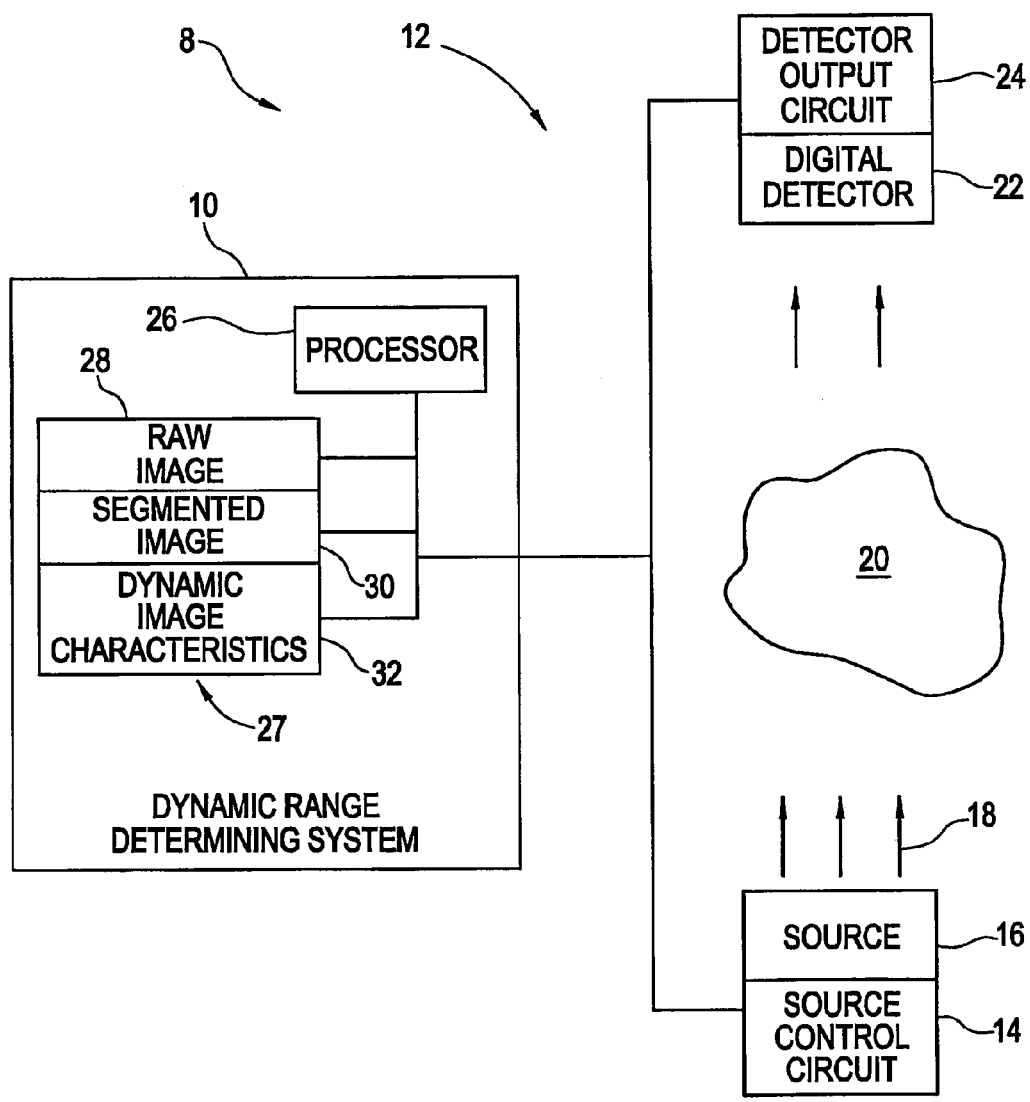
FIG. 1 illustrates a preferred embodiment of the present invention.

FIG. 1 illustrates a medical imaging system configured in accordance with the preferred embodiment of the present invention. The medical system 8 includes a dynamic range determining system 10 and a patient examining subsystem 12. The patient examining subsystem 12 includes a source 16 controlled by a control circuit 14. The source 16 emits a medium, such as radiation, through a patient 20. A digital detector 22 detects the medium 18 that passes through the patient 20. A detector output circuit 24 converts the information stored by the digital detector 22 to an electronic format processable by the processor 26 in the dynamic range control determining 10. The processor 26 accepts an input from the detector output circuit 24 and based thereon stores a raw digital image 28 in memory 27. The raw digital image 28 includes a clinical region and a non-clinical region.

The processor 26 distinguishes the non-clinical region from the clinical region in the raw image 28 in accordance with alternative techniques described below to form a segmented image 30. The segmented image 30 is stored in memory 27 and contains only the clinical region, with the non-clinical region being masked. Next, the processor 26 calculates the dynamic range of the clinical region in the segmented image 30 and based thereon generates dynamic range image characteristics 32. The dynamic range image characteristics 32 are stored in memory 26.

Figure 2:
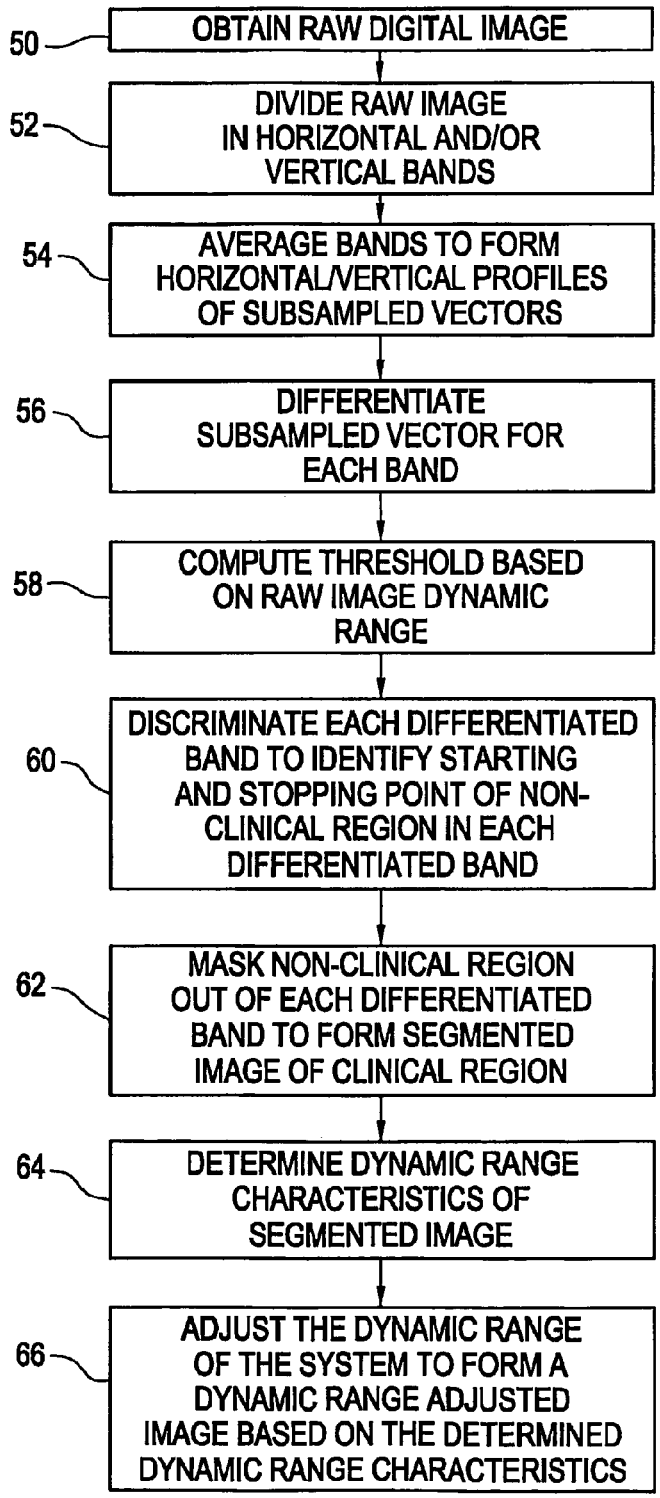
FIG. 2 illustrates a processing sequence carried out according to a preferred embodiment of the present invention.
Figure 3:
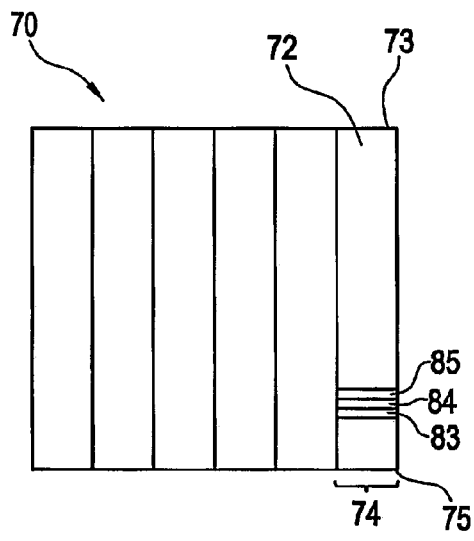
FIG. 3 illustrates a digital medical image divided in vertical bands generated in accordance with a preferred embodiment of the present invention.
Figure 4:
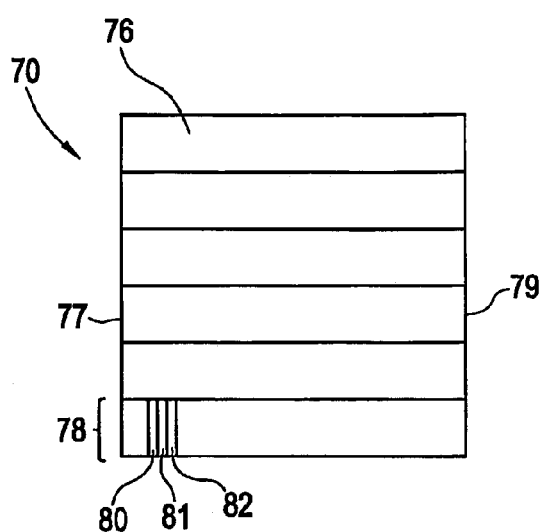
FIG. 4 illustrates a digital medical image divided into horizontal bands in accordance with a preferred embodiment of the present invention.

Turning to FIG. 2, a processing sequence is illustrated that may be carried out by the processor 26 in order to determine the dynamic range of the digital medical image. Beginning at step 50, the processor 26 obtains the raw digital image 28 either from detector 24 or memory 27. At step 52, the processor 26 divides the raw digital image 28 into horizontal and/or vertical bands of pixels. Exemplary bands are illustrated in FIGS. 3 and 4. FIG. 3 illustrates a raw digital image 70 which may be comprised of an array of pixel values, such as a 2K by 2K pixel array. The digital image 70 is divided at step 52 into a plurality of vertical bands 72 extending from the top 73 to the bottom 75 of the image and having a predetermined vertical bandwidth 74. By way of example only, each vertical bandwidth 74 may equal an even number of pixels, such as 100 in vertical band rows 83–85. Thus, in a 2000 by 2000 digital image 70, twenty vertical bands 72 would be utilized, each of which is 100 pixels in width.

Alternatively or in addition, at step 52, the digital image 70 may be divided into horizontal bands 76 as illustrated in FIG. 4. The horizontal bands 76 extend from the left side 77 to the right side 79 of the digital image 76 and have a predetermined horizontal bandwidth 78. By way of example, the horizontal bandwidth 78 may also be 100 pixels in width horizontal band columns 80–82. The horizontal bands 76 extend from one side of the digital image 70 to the other.

Once the horizontal and/or vertical bands 72, 76 are created in step 52, the processor 26 calculates an average gray scale pixel value across the width of each horizontal and vertical band 72 and 76 (step 54). By way of example, a horizontal band 78 may be 100 pixels in width and 2,000 pixels in length. At step 54, the processor sequentially steps through each set of 100 pixels in horizontal band columns 80–82. An average pixel value is calculated for the 100 pixels in horizontal band column 80, while separate average pixel values are calculated based upon the 100 pixel sets in horizontal band columns 81 and 82. This process is repeated until a subsampled vector is formed for each horizontal band 78. In the example of FIG. 4, each sub-sampled vector includes 2,000 average pixel values extending across the profile or length of the horizontal band 78. A separate sub-sampled vector is calculated for each horizontal band 78 and/or each vertical band 74. Once the sub-sampled vectors are calculated, a horizontal and/or vertical profile is generated for each horizontal and vertical band 74 and 78.

Figure 5:
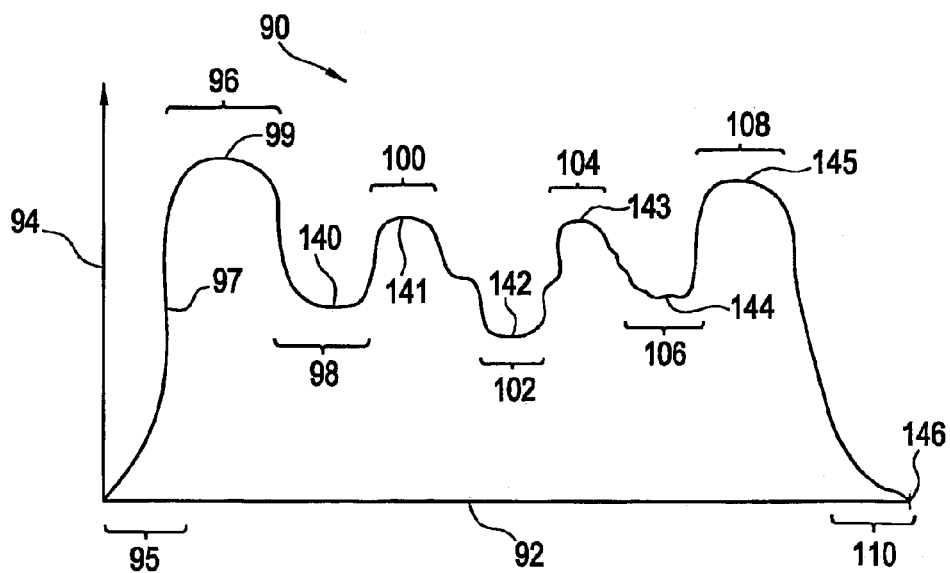
FIG. 5 illustrates a gray scale profile of a horizontal or vertical band of a digital medical image generated in accordance with a preferred embodiment of the present invention.

FIG. 5 illustrates graphically a profile 90 associated with an exemplary vertical or horizontal band 74 or 78. The horizontal axis 92 of the profile 90 in FIG. 5 corresponds to the length of an associated vertical or horizontal band 74 or 78. The vertical axis 94 corresponds to the gray scale levels of the average pixel values for a subsample vector associated with a grouping of pixels within one of rows 83–85 or columns 80–82 of an associated vertical or horizontal band 74 or 78, respectively. In the example discussed above, where a horizontal band 78 includes 2,000 pixels in length and 100 pixels in width, the associated profile 90 would include 2,000 average pixel values spanning the length of horizontal axis 92 of the profile 90.

The exemplary profile 90 of average pixel values illustrated in FIG. 5, may be from an x-ray scan of the chest of a patient. The profile 90 includes leading and trailing portions 95 and 110 having gray scale levels approaching zero. Leading and trailing portions 95 and 110 may correspond to regions of the detector covered by a collimator which blocks a majority of the radiation. Raw radiation peaks 96 and 108 correspond to areas having high exposure to radiation and may simply represent raw radiation exposed to the digital detector. Tissue valleys 98 and 106 correspond to tissue portions of the patient such as along the left and right sides of the chest. Intermediate lung peaks 100 and 104 correspond to the lungs of the patient, while mediastinum valley 102 corresponds to the center or mediastinum of the patient.

Figure 6:
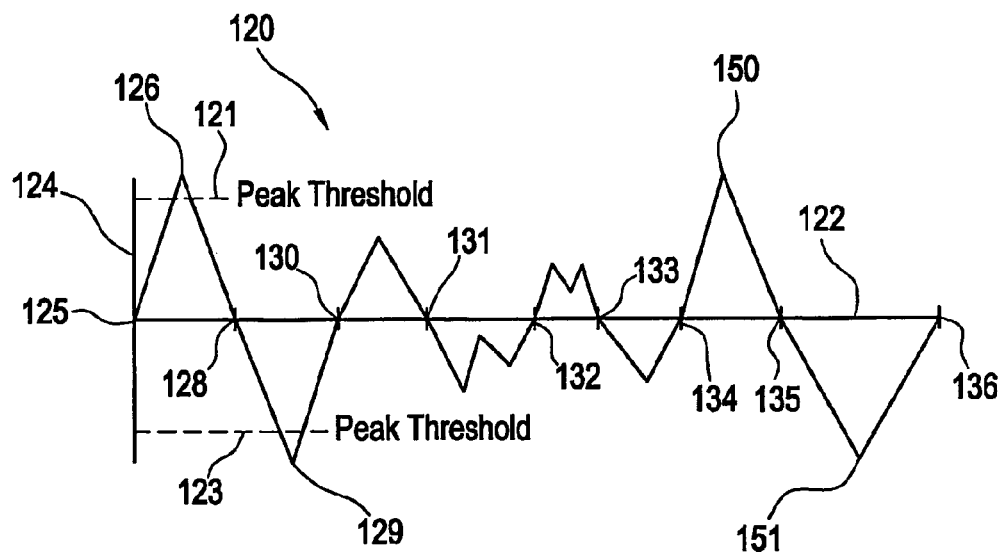
FIG. 6 illustrates a differentiated gray scale profile associated with the profile of FIG. 5 generated in accordance with a preferred embodiment of the present invention.

Once the profile 90 has been generated, the profile 90 of the sub-sample vector for each band is differentiated at step 56 to obtain a differentiated gray scale profile identifying the change in gray scale at each location along profile 90. FIG. 6 illustrates a differentiated gray scale profile 120 with the horizontal axis 122 corresponding to a length of an associated vertical or horizontal band 74 or 78. The vertical axis 124 of the differentiated gray scale profile 120 identifies positive and negative changes in the gray scale level per unit distance along an associated band 72, 74. For example, peak 126 is associated with the point 97 of profile 90 having a maximum slope. The peak 99 in the raw radiation portion 96 corresponds to point 128 in the differentiated gray scale profile 120, where the differentiated gray scale equals zero. The points 130–136 at which the differentiated gray scale profile 120 cross zero correspond to points 140–146 in the gray scale profile 90, respectively.

Next, at step 58 in FIG. 2, the processor 26 calculates thresholds that may be utilized to identify peaks in the differentiated gray scale profile 120. At step 60, the processor 26 discriminates each differentiated band to identify starting and stopping points of non-clinical regions, such as associated with raw radiation and collimators. By way of example only, a raw radiation search algorithm may be carried out to analyze the differentiated gray scale profile 120 to identify the starting and stopping points of the non-clinical regions.

As an example, the processor 26 may begin by scanning the differentiated gray scale profile 120 from left to right and identify the first positive peak 126 of the profile 120. Once peak 126 is identified, the processor 26 reverses scanning direction and searches toward the left edge of the profile 120 until the processor 26 identifies a point where differentiated vector equals zero. The processor 26 then turns on a mask in the digital image 28 at the point corresponding to the point where the differentiated vector equals zero (namely point 125). Next, the mask remains on as the differentiated profile is scanned for the first negative peak (point 129). Peaks 126 and 129 may be identified by comparing the peak thresholds 121 and 123 to the differentiated profile 120. Once negative peak 129 is identified, the processor 26 continues scanning the differentiated vector until it equals zero (namely point 130). The mask is turned off at point 130.

The processor 126 continues to scan the differentiated profile 120 until the profile 120 again exceeds the positive peak threshold 121 (such as at point 150). When peak 150 is identified, the processor 26 reverses scanning direction to search until it identifies the point where the differentiated vector equals zero (point 134) and again turns on the mask. Scanning again continues to the right while the processor 26 searches for a negative peak which exceeds the threshold 123 (such as at point 151). Once negative peak 151 is identified, the differentiated vector 120 is then scanned for the next point at which it equals zero (point 136). At point 136, the mask is again turned off.

The foregoing discrimination technique effectively removes the portion of the digital medical image preceding point 130 and following point 134.

Turning to FIG. 5, the above discussed discrimination technique has the effect of removing or ignoring the portion of the digital medical image preceding point 140 and following point 144. The processor effectively identifies everything preceding point 140 and following point 144 to correspond to non-clinical regions, namely raw radiation and collimator regions. The remaining section of the profile 90 between points 140 and 144 include lung peaks 100 and 104 which correspond to the lungs and a mediastinum valley 102 which corresponds to the mediastinum. The region of the profile 90 between points 140 and 144 corresponds to the segmented image 30 stored in memory 27 in the dynamic range determining system 10.

Next, at step 64, the processor 26 computes desired image characteristics, such as mean, median, average, standard deviation, maximum and minimum gray scale values of the segmented image 30 and the like. As shown in FIG. 5, the maximum and minimum gray scale values correspond to points 141–143 and define the dynamic range of the clinical region. After determining the desired image characteristics, such as maximum and minimum gray scale values of the segmented image 30, in step 66, the processor 26 adjusts the dynamic range of the medical diagnostic imaging system to form a dynamic range adjusted image based on the image characteristics. The dynamic range adjusted image and/or dynamic range image characteristics 32 are stored in memory 26.

Optionally, the dynamic range adjusted image may be obtained by mapping the clinical region of the original raw digital image 28 into an output image segment by passing the clinical region of the raw digital image 28 through a look-up table that correlates input pixel values to desired output pixel values. For instance, the input and output pixel values stored in the look-up table may have a linear relation to one another, a sigmoidal relation to one another and the like. The image characteristics, such as maximum and minimum gray scale values, calculated at step 64 may be utilized to adjust the slope or shape of the mapping function in the look-up table, in order to maintain a constant dynamic range for all digital images processed by the system regardless of variations in film, patients, exposure and systems.

It should be noted that not all digital medical images include non-clinical regions. Hence, at step 60, the discrimination may have a null or empty solution (e.g., no starting and stopping points). Digital medical images that do not include non-clinical regions will be treated in step 64 as the segmented image. Step 62 will effectively be skipped.

Figure 7:
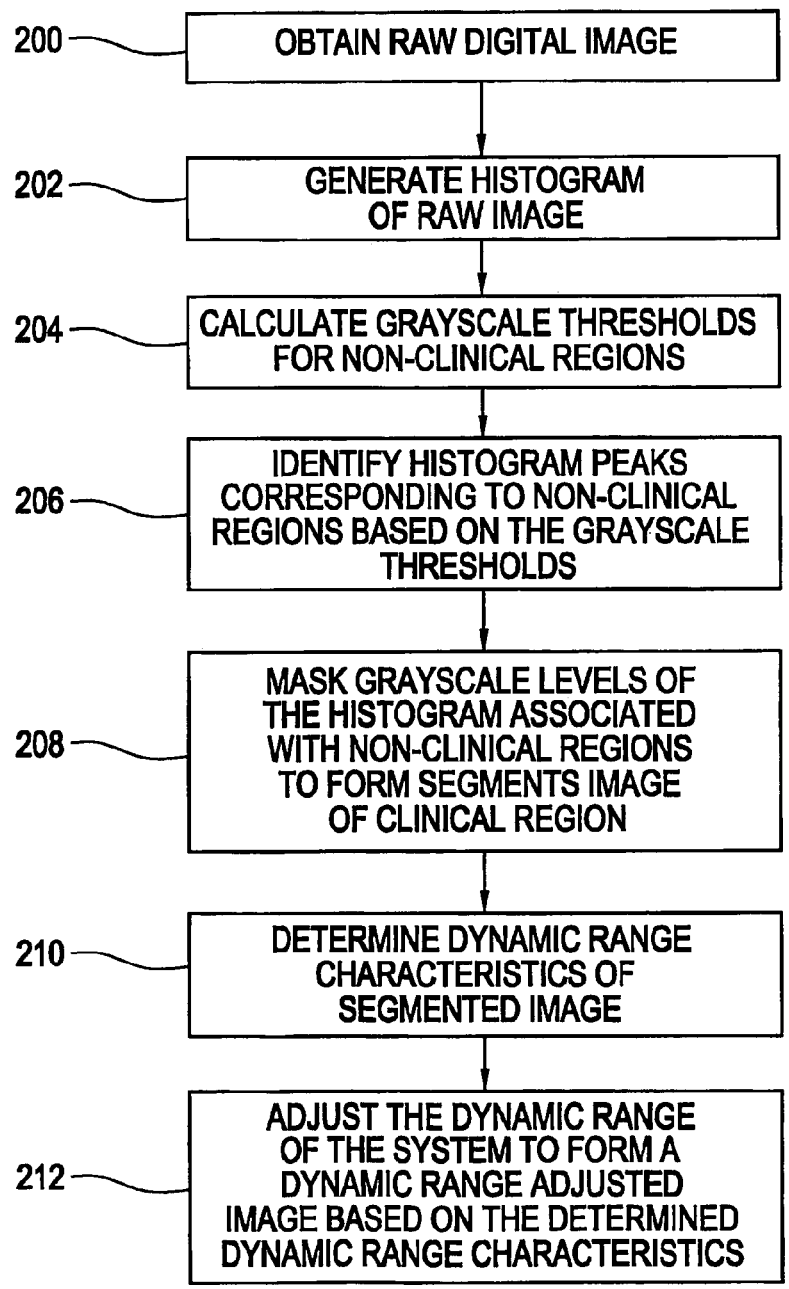
FIG. 7 illustrates a processing sequence carried out in accordance with an alternative embodiment of the present invention.

Next, the discussion turns to an alternative embodiment for segmenting non-clinical regions, as illustrated in FIG. 7. Beginning at step 200, the processor 26 again obtains a raw digital image 28. A histogram is generated at step 202 from the raw digital image 28. At step 204, gray scale thresholds are calculated for gray scale levels within the histogram associated with non-clinical regions. At step 206, the gray scale thresholds are used to identify peaks in the histogram which correspond to the non-clinical regions. Once the non-clinical regions are identified in step 206, the gray scale levels of the histogram that are associated with the non-clinical are masked and the remaining gray scale levels from the digital image form a segmented image 30 corresponding to the clinical region. At step 210, the processor determines dynamic range characteristics for the segmented image 30. At step 212, the dynamic range of the medical diagnostic imaging system is adjusted to form a diagnostic range adjusted image based on the dynamic range characteristics calculated in step 210.

Figure 8:
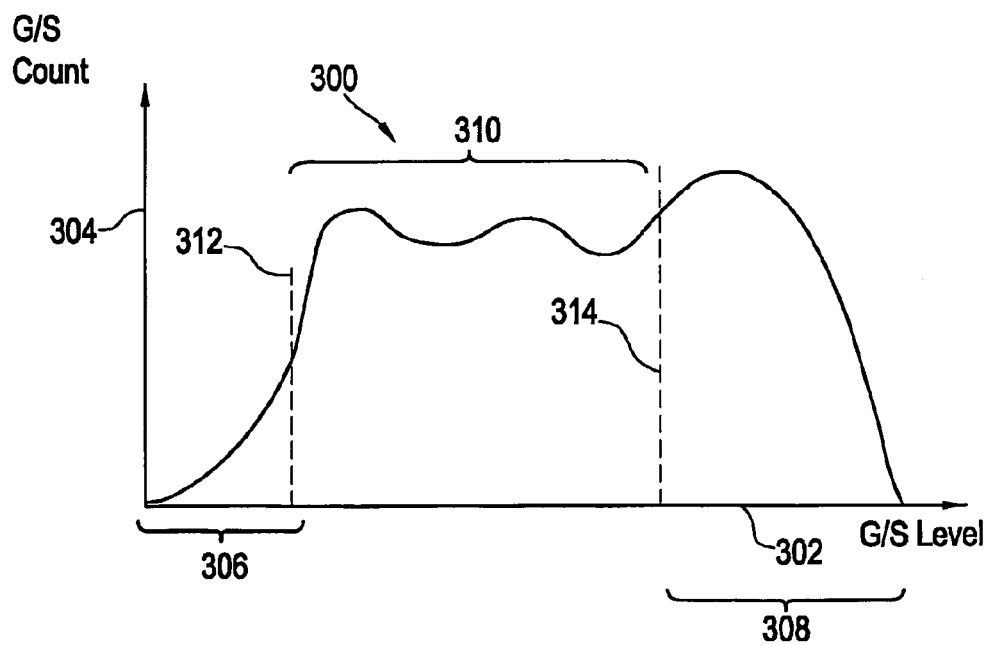
FIG. 8 illustrates a gray scale histogram generated in accordance with an alternative embodiment of the present invention.

The processing sequence of FIG. 7 is better illustrated in connection with FIG. 8. FIG. 8 illustrates a histogram 300 generated at step 202, in which the gray scale levels are denoted along the horizontal axis 302 and the count of pixels at each gray scale level is denoted along the vertical axis 304. The histogram 300 includes a leading region 306 having gray scale levels that are very low. Portion region 306 may correspond to a collimator region. The histogram 300 further includes a trailing region 308 having a large number of pixels at very high gray scale levels. Region 308 may correspond to raw radiation regions of the digital image 28. An intermediate region 310 corresponds to the clinical region containing the gray scale levels associated with the lungs and mediastinum.

During operation, gray scale thresholds 312 and 314 are calculated at step 204 and used to identify peaks corresponding to non-clinical regions (i.e., regions 306 and 308). At step 208, the gray scale levels in regions 306 and 308 are masked to hide associated non-clinical regions, and to form a segmented image 30 containing only clinical regions have gray scale values from intermediate region 310. Next, at step 210, the maximum and minimum gray scale values within intermediate region 310 are calculated and used to adjust the dynamic range of the medical system at step 212.

The dynamic range management system of the preferred embodiments enables desired output optical densities to be obtained for all patients, regardless of the type of film, screen or detector used, regardless of the exposure, regardless of the dose and regardless of the individual patient being scanned.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

The invention claimed is:

1. A method for determining a dynamic range of a digital medical image for a medical imaging system, the digital medical image containing a clinical region, comprising:
   dividing a digital medical image into at least two bands of predetermined width;
   generating a profile for each of said at least two bands of predetermined width;
   determining whether the digital medical image within said at least two bands includes at least one non-clinical region based on said profile;
   masking said at least one non-clinical region based on at least one of gray scale maximum and minimum values for the at least one non-clinical region, said at least one non-clinical region comprising one of a raw radiation region and a collimated region; and
   calculating a dynamic range based on a clinical region within each of said at least two bands.

2. The method of claim 1, wherein the dividing step further comprises dividing the digital medical image into one of horizontal and vertical bands.

3. The method of claim 1, further comprising:
differentiating said digital medical image, said determining step calculating a position of the non-clinical region based on a result of said differentiation.

4. The method of claim 1, further comprising:
calculating at least one threshold based on a dynamic range of the digital medical image, said at least one threshold being used to identify at least one of maximum and minimum values for the non-clinical region.

5. The method of claim 1, wherein said determining step discriminates at least one of histogram maximum and minimum values for a non-clinical region based on at least one predetermined threshold.

6. The method of claim 1, further comprising:
when a non-clinical region is determined to exist, masking the non-clinical region from the digital medical image before calculating said dynamic range.

7. The method of claim 1, further comprising:
generating a histogram of the digital medical image; and masking gray scale levels from the histogram that exceed predetermined upper and lower thresholds.

8. The method of claim 1, wherein said determining step determines that the digital medical image does not include a non-clinical region and said calculating step calculates a dynamic range of the entire digital medical image as the clinical region.

9. The method of claim 1, further comprising differentiating said digital medical image, said determining step calculating positions of first and second non-clinical regions based on a result of said differentiation, said first and second non-clinical regions comprising raw radiation data and collimated data, respectively.

10. A medical diagnostic imaging system for controlling a dynamic range of a digital medical image to be displayed, comprising:
a segmentation module identifying clinical and non-clinical regions within a digital medical image, said non-clinical regions comprising at least a collimated region;
a processor dividing the digital medical image into at least two bands, wherein said processor is capable of masking at least one non-clinical region based on at least one of gray scale maximum and minimum values for the at least one non-clinical region, the at least one non-clinical region comprising at least one of a raw radiation region and a collimated region; and
a dynamic range module determining a dynamic range of a clinical region of the digital medical image based on the clinical region, said dynamic range module determining a dynamic range of said clinical region within said at least two bands, said dynamic range module computing dynamic range characteristics based on said dynamic range, said dynamic range characteristics capable of adjusting said digital medical image.

11. The system of claim 10, further comprising a digital detector obtaining said digital medical image having said clinical and non-clinical regions.

12. The system of claim 10, wherein the segmentation module identifies said non-clinical regions based on variations in gray scale levels of the digital medical image.

13. The system of claim 10 wherein the segmentation module differentiates at least a portion of the digital medical image to identify the non-clinical regions.

14. The system of claim 10, wherein the segmentation module discriminates the non-clinical regions based on at least one gray scale threshold value.

15. The system of claim 10, further comprising a processor calculating at least one threshold based on a dynamic range of the digital medical image, said segmentation module discriminating the non-clinical regions based on said threshold.

16. The system of claim 10, said dynamic range module including a processor masking over said non-clinical regions when determining the dynamic range of the clinical region.

17. The system of claim 10 further comprising a processor calculating at least one of a maximum and minimum gray scale level for the digital medical image in order to identify the non-clinical regions.

18. The system of claim 10, further comprising a processor calculating at least one of maximum and minimum gray scale levels for the clinical region in order to determine the dynamic range of the clinical region.

19. The system of claim 10, further comprising a processor generating a histogram of at least a portion of the digital medical image to identify gray scale levels associated with said non-clinical regions.

20. The system of claim 10, wherein the segmentation module masks said non-clinical regions identified in the digital medical image.

21. The system of claim 10, wherein the segmentation module determines that the digital medical image does not include said non-clinical regions, said dynamic range module using the digital medical image to determine said dynamic range of the digital medical image.

22. The system of claim 10, further comprising a processor dividing said digital medical image into at least two hands, wherein said at least two bands comprise one of horizontal and vertical bands, said dynamic range module determining a dynamic range of said clinical region within said at least two bands.

* * * * *